US008036997B2

(12) United States Patent
Garrity et al.

(10) Patent No.: US 8,036,997 B2
(45) Date of Patent: Oct. 11, 2011

(54) METHODS FOR DATA CLASSIFICATION

(75) Inventors: George Garrity, Okemos, MI (US);
Timothy G. Lilburn, Front Royal, VA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 496 days.

(21) Appl. No.: 11/922,273

(22) PCT Filed: Jun. 16, 2006

(86) PCT No.: PCT/US2006/023381
§ 371 (c)(1),
(2), (4) Date: Apr. 2, 2009

(87) PCT Pub. No.: WO2006/138502
PCT Pub. Date: Dec. 28, 2006

(65) Prior Publication Data
US 2009/0299926 A1    Dec. 3, 2009

Related U.S. Application Data

(60) Provisional application No. 60/690,969, filed on Jun. 16, 2005.

(51) Int. Cl.
*G06F 15/18* (2006.01)
(52) U.S. Cl. ........................................................ 706/13
(58) Field of Classification Search ................... None
See application file for complete search history.

(56) References Cited

U.S. PATENT DOCUMENTS

| 5,870,729 | A | * | 2/1999 | Yoda ............................... 706/26 |
| 2004/0234995 | A1 | * | 11/2004 | Musick et al. ..................... 435/6 |
| 2005/0010541 | A1 | * | 1/2005 | Rietman ........................... 706/12 |

* cited by examiner

*Primary Examiner* — Jeffrey A Gaffin
*Assistant Examiner* — Paulinho Smith
(74) *Attorney, Agent, or Firm* — Medlen & Carroll, LLP

(57) ABSTRACT

The present invention provides methods for classifying data and uncovering and correcting annotation errors. In particular, the present invention provides a self-organizing, self-correcting algorithm for use in classifying data. Additionally, the present invention provides a method for classifying biological taxa.

9 Claims, 7 Drawing Sheets

METHODS FOR DATA CLASSIFICATION

The present invention claims priority to U.S. Provisional Patent Application No. 60/690,969, filed Jun. 16, 2005, hereby incorporated by reference in its entirety.

This invention was funded, in part, under the Biological and Environmental Research Program (BER), United States Department of Energy, Grant No. DE-FG02-02ER63315. The government may have certain rights in the invention.

FIELD OF THE INVENTION

The present invention provides methods for classifying data and uncovering and correcting annotation errors. In particular, the present invention provides self-organizing, self-correcting methods, systems, and algorithms for use in classifying data. Additionally, the present invention provides a method for classifying biological taxa.

BACKGROUND OF THE INVENTION

Principal component analysis (PCA) is a classical statistical method. This linear transform is widely used in data analysis and compression. PCA involves a mathematical procedure that transforms a number of possibly correlated variables into a smaller number of uncorrelated variables called principal components. The first principal component accounts for as much of the variability in the data as possible, and each succeeding component accounts for as much of the remaining variability as possible. The objective of PCA is to discover or to reduce the dimensionality of a data set and to identify new meaningful underlying variables.

PCA has been used to analyze complex data, including phylogenetic data used to classify organisms. The principal method of establishing phylogenetic relationships among prokaryotic organisms is through analysis of SSU rRNA. Currently, over 125,000 organism specific SSU rRNA sequences are publicly available. Exploratory data analysis methods such as principal components analysis techniques indicate higher order relationships among SSU rRNA sequences similar to the July 2002 Bergey's taxonomy. However, principal components analysis techniques fail to provide undistorted visual presentation of the orderings, and fail to provide automated identification and re-placement of classification errors.

The simple act of naming and classifying an entity (e.g., biological entity) that is part of a large, complex classification system has potentially far-reaching and long-lived consequences. Names, especially those ascribed to organisms, serve as a primary entry point into the scientific, medical, and technical literature and figure prominently in countless laws and regulations governing various aspects of commerce, public safety and public health. Biological names also serve as a primary entry point into many of the central databases that the scientific community and the general public rely upon. However, ascribed names do not govern the process of biological classification or identification, rather, only the formation and assignment of names to proposed taxa. Hence, legitimate and valid names may be ascribed to poorly formed taxa and illegitimate and invalid names may be assigned to well-formed taxa.

A disjunction between nomenclature and taxonomy leads to an accumulation of dubious names in the literature and databases. From a practical, legal, or regulatory sense, incorrect classification can have significant and unintended consequences. For example, these errors may lead to adding or removing biological species to lists of tightly regulated organisms such as the current list of biothreat agents in the United States or organisms restricted by packaging and shipping regulations.

What is needed is an improved visual presentation of data classifications generated from principal components analysis based orderings, and a method of providing automated identification and re-placement of classification errors. Additionally, there is a need for a system of nomenclature and classification of biological taxa and other similar data sets that takes advantage of the large numbers of SSU rRNA sequences or corresponding identifiers available, that is reconcilable with other knowledge concerning genotypic and phenotypic information.

SUMMARY OF THE INVENTION

The present invention provides methods for classifying data. In particular, the present invention provides a self-organizing, self-correcting algorithm for use in classifying data. Additionally, the present invention provides a method for classifying biological taxa.

Accordingly, the present invention provides a method of classifying data by providing a data set, wherein the data set comprises unique data points, a self-organizing, self-correcting algorithm, and software, wherein the software is configured to run the self-organizing, self-correcting algorithm; inputting the data set into the algorithm; generating a classification of the data set, wherein the generating a classification of the data set comprises: removing data points not meeting a predetermined similarity criteria, generating a first classification, wherein the first classification comprises a first classification plurality of groupings, wherein the first classification plurality of groupings comprise data points meeting the predetermined similarity criteria that are related, fitting the data points not meeting a pre-determined similarity criteria into the first classification, and; generating a second classification, wherein the second classification comprises a second classification plurality of groupings, wherein the second classification plurality of groupings comprise related data points meeting a pre-determined similarity criteria and data points not meeting a pre-determined similarity criteria. In some embodiments, the predetermined similarity criteria comprises a $90^{th}$ percentile goodness-of-fit value. In some embodiments, the method further comprises the step of subjecting groups of data to a medioid algorithm.

In some embodiments, the method of classifying data further comprises visualizing the classification of the data. For example, in one embodiment, the present invention provides visualizing the classification of the data set through display of a heat map.

The present invention is not limited by the nature of the data used in the systems and methods. In some embodiments, the data comprises biological data (e.g., information pertaining to an organism identity, patient information, sociological characteristics of an organism, etc.). In some embodiments, the data comprises non-biological scientific data (e.g., data corresponding to properties of materials, chemicals, drugs, celestial bodies, biometric measurements, etc.). In some embodiments, the data comprises financial data (e.g., characteristics of a company, traded security, etc.).

In a preferred embodiment, the data set classified by the systems and methods of the present invention comprises prokaryotic SSU rRNA sequences. In still further preferred embodiments, each of the prokaryotic SSU rRNA sequences are specific for a prokaryotic organism. In other embodiments, the data set classified by the systems and methods of the present invention comprises prokaryotic nucleic acid or peptide sequences, eukaryotic nucleic acid or peptide sequences, viral nucleic acid or peptide sequences, nucleic acid or peptide sequences generated from cell lines, or nucleic acid sequences encoding enzymes, catalytic nucleic acid molecules, small nucleic acid molecule inhibitors, etc.

In some embodiments, the method of classifying data further comprises identifying the classification of an unknown data point, wherein identifying the classification of an unknown data point comprises inputting the unknown data point into the algorithm and fitting the unknown data point into the second classification. In some embodiments, the unknown data point is an unknown SSU rRNA sequence.

DEFINITIONS

Figure 1:
FIG. 1 shows an exemplary heat map of the "Gammaproteobacteria" based on an evolutionary distance matrix with unnamed and uncorrected sequences removed.

To facilitate an understanding of the present invention, a number of terms and phrases are defined below:

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "encode" refers to the process of converting one type of information or signal into a different type of information or signal to, for example, facilitate the transmission and/or interpretability of the information or signal. For example, image files can be converted into (i.e., encoded into) electrical or digital information. Likewise, light patterns can be converted into electrical or digital information that provides an encoded video capture of the light patterns.

As used herein, the term "in electronic communication" refers to electrical devices (e.g., computers, processors, etc.) that are configured to communicate with one another through direct or indirect signaling. For example, a conference bridge that is connected to a processor through a cable or wire, such that information can pass between the conference bridge and the processor, are in electronic communication with one another. Likewise, a computer configured to transmit (e.g., through cables, wires, infrared signals, wireless signals, telephone lines, etc) information to another computer or device, is in electronic communication with the other computer or device.

As used herein, the term "transmitting" refers to the movement of information (e.g., data) from one location to another (e.g., from one device to another) using any suitable means.

DETAILED DESCRIPTION OF THE INVENTION

The present invention provides methods for classifying data. In particular, the present invention provides a self-organizing, self-correcting algorithm for use in classifying data. Additionally, the present invention provides a method for classifying biological taxa.

The following description illustrates the invention using biological examples. It should be understood that the present invention is not limited to the classification, organization, and correction of biological data.

1. Self-Organizing, Self-Correcting Algorithm.

Principal component analysis (PCA) is widely used in data analysis, compression and classification. The objective of PCA is to discover or to reduce the dimensionality of a data set and to identify new meaningful underlying variables. One shortcoming of algorithms written for PCA is that they force-fit data into classifications, potentially skewing proper grouping of data and making interpretation of the data difficult. Additionally, there currently exists poor visual presentation of data classifications generated from principal components analysis based orderings, and a method of providing automated identification and relocation of classification errors has not been forthcoming.

The present invention cures these defects. In particular, in some embodiments, the present invention provides a self-organizing, self-correcting classification algorithm created and used to dynamically record data organizations (e.g., heat maps) to automatically generate classifications, review and modify the classifications, identify possible classification errors, facilitate ad-hoc testing of alternative classifications/hypothesis, and correctly classify new entries (e.g., See Example 1). In some embodiments, although hierarchical clustering techniques are employed, the algorithm circumvents the force fitting of data into a hierarchy. Rather, in some embodiments, the algorithm provides a means of identifying and selectively excluding data points that fail to meet minimal criteria for group membership, thereby permitting "good" clusters to form. The excluded data sets can then be added back to the global model to allow for a more precise placement if possible. In addition, since hierarchical clustering techniques are used on a localized level, the effect of evolutionary rate variability across disparate entities (e.g., widely divergent taxa) is minimized, leading to classifications that are consistent with established phylogenetic models.

The present invention is not limited by the type of data applied to (e.g., examined or interrogated by) the algorithm of the present invention. Indeed, a variety of data sets can be analyzed. In some embodiments, the data set comprises prokaryotic SSU rRNA sequences. In further embodiments, each SSU rRNA sequence is specific for a prokaryotic organism. For example, the method of classifying data can be used to create, from an extant class of bacteria, an ordered and revised hierarchical taxonomy (e.g., in a short amount of time (e.g., in approximately twenty minutes (e.g., See Examples 2-4, 9))). In still further embodiments, the algorithm is used to classify other data sets, including, but not limited to, prokaryotic nucleic acid or peptide sequences, eukaryotic nucleic acid or peptide sequences, viral nucleic acid or peptide sequences, nucleic acid or peptide sequences generated from cell lines, or nucleic acid sequences encoding enzymes, catalytic nucleic acid molecules, small nucleic acid molecule inhibitors, and other data sets. For example, it is contemplated that the method of classification of the present invention can be used to identify and classify genes involved in oncogenesis, tumorogenesis, metastasis, drug response, cell death, angiogenesis, etc.

Although the previous examples are focused on the problem of biological classification, the algorithm is not limited to use solely in taxonomy and biological classification. Indeed, the algorithm of Example 1 is applicable to any classification for which a metric exists or can be derived. For example, the algorithm of the present invention, with its automated identification and re-placement of classification errors, is contemplated to be useful in the dynamic recording of heat maps to automatically generate, review and modify the classification of securities, certificates, secured transactions, sales receipts, or other types of recorded data.

In some embodiments, the method of classifying data of the present invention is used to identify the classification of an unknown data point through inputting the unknown data point into the algorithm. In some embodiments, the unknown data point is an unknown SSU rRNA sequence (e.g., See Examples 6-8). Additionally, it is contemplated that any unknown data point for which a metric exists or for which a metric can be derived can be classified using the algorithm of the present invention.

EXPERIMENTAL

The following examples are provided in order to demonstrate and further illustrate certain preferred embodiments and aspects of the present invention and are not to be construed as limiting the scope thereof.

Example 1

Self-Organizing, Self-Correcting Algorithm

Algorithm. The algorithm is implemented in the S programming language (See, e.g., Becker et al., The new S language: a programming environment for data analysis and graphics, Wadsworth & Brooks/Cole Advanced Books & Software, Pacific Grove, Calif., (1988)) and relies on functions that are part of the S-Plus environment (Version 6.1; Insightful, Seattle, Wash.). The code developed is available as an S-Plus script and can be implemented, with some modifications, in R (See, e.g., Venables and Smith, An Introduction to R, Network Theory Ltd., Bristol, UK (2002)).

Data. Data analyzed during development of the present invention consisted of 1433 sequences that were initially classified as belonging to the "Gammaproteobacteria". The sequences were aligned and an evolutionary distance matrix was prepared as described in Garrity and Lilburn (See, e.g., Garrity and Lilburn, WFCC Newsletter, 35, 5-15 (2002)) except that a fully reflected distance matrix was used rather than the rectangular benchmarked matrix. Sequences were obtained from the RDP-II database (See, e.g., Cole et al., Nucleic Acids Res., 31:442 (2003)) and from Genbank. The Taxonomic Outline of the Procaryotes is available in pdf format at dx.doi.org/10.1007/bergeysoutline.

---

STEP 1. Data input
Read distance matrix (ASCII file) into S-plus matrix (DIST.MAT)
    DIST.MAT is the output from PAUP
Create corresponding taxonomy S-Plus data.frame from master taxonomy data.frame (TAX.TABLE)
    TAX.TABLE initially contains three columns (as factor variables): the species name, the numerical position of
    the species in the current version of Bergey's Taxonomic Outline, and the corresponding famly to which the
    species is assigned with the current version of the taxonomy.
NOTE - each data element (16S rDNA distance vector or corresponding taxonomy vector) is uniquely identified by the
RDP ID.
    This identifier serves as a pointer for indexing into data structures.
Sort distance matrix according to Bergey's Outline Sequence
Visualize the DIST.MAT as a heat map
STEP 2. Reorder DIST.MAT (first pass)
NOTE - the goal at this stage of the analysis is to examine DIST.MAT at the genus level, to identify any
    potential misplacements that arise because of misidentificaiton of sequences or because of a failure to identify
    synonyms and update the nomenclature associated with such sequences.
Create a vector of genus names for each sequence (GENUS.NAME)
Create a vector of unique genus names (TAXON.LEVEL)
Initialize an S-Plus list for storing RDP-Ids for each unique genus, attach the corresponding name to each
    list element (TAXON.SEQ.NEW)
FOR each unique genus name
    IF two or less representative sequences exists for a given genus
        add RDP-Ids to the corresponding element in TAXON.SEQ.NEW
    ENDIF
    IF more than two representative sequences exist for a given genus
        extract the genus-level sub matrix from DIS.MAT and assign to TEMP.DIS
        IF sum of the matrix == 0
        add RDP-Ids to the corresponding element in TAXON.SEQ.NEW
        NEXT
        NOTE - This step is important to avoid failure of subsequent clustering
    ENDIF
    Jitter the matrix to eliminate ties

```
    FOR each row in TEMP.DIS
        determine the rank-order of the evolutionary distance values
        store in TEMP.ORDER
    NEXT
    FOR each column in TEMP.ORDER
        identify the name of the top-ranked sequence, add to TEMP.REORDER
    NEXT
    Identify any names dropped because of a tie-score for top-ranking (DROPPED.NAMES)
    Reorder TEMP.DIS according to merged name vector (TEMP.REORDER, DROPPED.NAMES)
    Reorder TEMP.ORDER according to merged name vector (TEMP.REORDER, DROPPED.NAMES)
    NOTE - at this point a mask based on a sample-based threshold score of the second-best match is created.
        This value is used to eliminate the problem of artificially low values arising from self-matching. This
        next series of steps involve vectorized operations on TEMP.ORDER and TEMP.DIS to extract indices
        and values in a single step.
    IF a second-best matches are found with TEMP.ORDER
        Calculate the threshold value (default currently set to 90%ile) from
        Corresponding vales in TEMP.DIS
    ENDIF
    IF a second-best matches are not found within TEMP.ORDER (this can occur when
        ties exist in TEMP.ORDER)
        calculate the threshold value (default currently set to 90%ile) from
        corresponding values in TEMP.DIS ranked at >1 and <2.
    ENDIF
    Create a logical matrix of neighbors (NEIGHBORHOOD) in which values > 90%ile set to T
    Recast NEIGHBORHOOD as binary matrix
    Multiply TEMP.DIS by NEIGHBORHOOD to create a mask of nearest neighbors
    Hierarchical Binary clustering of NEIGHBORHOOD along both dimensions
        NOTE - current model employs binary distance matrix, complete linkage and
            Reordering of the resulting model according to mean evolutionary
            Distance of each sequence in TEMP
        Reorder TEMP.DIS along both dimensions according to the cluster analysis
    ENDIF
NEXT
Create new index into DIST.MAT from TAXON.SEQ.NEW
Plot heat map
NOTE - At this point, misidentified sequences can be visualized in the matrix and can be identified
    through interactive visualization of the distance matrix in the heat map viewer.
STEP 3. - Removal of misidentified sequences
Restructure DIS.MAT based along TAXON.SEQ.NEW
Create modified version of TAXON.SEQ.NEW (TAXON.SEQ.NEW2) by removal of misidentified
    sequences identified in heat map
Create new index into DIST.MAT from TAXON.SEQ.NEW2
Plot heat map
STEP 4. - Repeat STEP 2 with misidentified strains removed
STEP 5. - Visualization of revised DIST.MAT with Misidentified sequences
NOTE - this matrix is simply created by combining the revised index created from TAXON.SEQ.NEW
    and the index of misidentified sequences.
STEP 6. - Matching of unknown/misidentified strains to known strains
NOTE - This analysis requires the use of partial matrixes to allow matching of the unidentified or misidentified sequences
to its
    nearest neighbor
Create ID.MAT (DIS.MAT [ (misidentified, excluded sequence), correct sequence ])
Jitter matrix to eliminate ties
FOR each row in ID.MAT
    determine the rank-order of the evolutionary distance values
    store in TEMP.ORDER
NEXT
FOR each column in TEMP.ORDER
    Create ordered matrix of evolutionary distances (TEMP.ORDER)
NEXT
Identify any names dropped because of a tie-score for top-ranking (DROPPED.NAMES)
Reorder TEMP.DIS according to merged name vector (TEMP.REORDER, DROPPED.NAMES)
Remove known errors
    NOTE - when working below the domain level, there are valid reasons for dropping sequences that are known to
    be in
        error that would otherwise skew/distort the data.
FOR each sequence
    identify name of the correctly identified sequence that is closest in the unknown or misidentified sequence
    (BEST.MATCH)
NEXT
Create a dataframe (NEAREST.NEIGHBORS) from the row names of TEMP.ORDER and
    columns 1 and 2 of TAX.TABLE, indexed along BEST.MATCH. Then, add a column of genus names
    based on those appearing in the species names in column 1. Add appropriate column headers to
    columns 4 and 5.
Create a revised taxonomy table in which each sequence will be added back according to the best
    Match of a correctly identified sequence. (REVISED.TAX.TABLE)
STEP 7. - Reorder the complete distance matrix with the "identified" sequences added back
Restructure DIST.MAT based on REVISED.TAX.TABLE
Repeat STEP 2
```

-continued

```
STEP 8. - Outlier detection
NOTE - As is the case in a clustering routine, sequences that are clearly outside of a group will be added back to the group
with
    which closest affiliation is found unless some mechanism is included to identify those which exceed a threshold
    based on sample statistics. In this case, the sample statistics will be set to an evolutionary distance > 3 stdev
    above or below that of other members of a genus (TAXON.LEVEL)
FOR each instance in TAXON.LEVEL
    IF number of taxon members >= 4
        NOTE - this step is beneficial so as to have reasonable minimal sample size of 6 non-reflected values
        Create a temporary distance matrix (TEMP.REF)
        Create a vector (OUTLIER) of evolutionary distance that fall below 3*stdev of the lower triangle of
            TEMP.REF
        Create a matrix (TEMP2) of logical values (as 0,1) that identify where the values in OUTLIER occur
        Calculate row sums for TEMP2 to identify which taxa are outliers
        Extract names of outliers from TEMP2 for those rows in which the row sum > 3Q of TEMP2
    ENDIF
NEXT
Identify outliers in REVISED.GAMMA.TAX by setting the MPI species and family to "placement error"
STEP 9. - Resolution of placement errors
Create ID.MATRIX for sequences identified as placement errors
Assign ID.MATRIX to TEMP
Repeat STEP 6
STEP 10. - Add back mislabeled strains
Re-create REVISED.TAX.TABLE from REVISED.TAX.TABLE (placement errors excluded) and
NEAREST.NEIGHBORS
    NOTE - data frame built in row-wise fashion
Recreate GENUS.NAMES and TAXON.LEVEL as in STEP-2
Reorder DIST.MAT by REVISED.TAX.TABLE
Repeat STEP 2
STEP 11.- Calculation of genus medioids
Restructure DIST.MAT along both dimensions by TAXON.SEQ.NEW in STEP 10
Recreate vector of GENUS.NAMES
Create TAXON matrix (GENUS NAME x unique (GENUS.NAME))
Create TAXON.NAMES (=unique(GENUS.NAME)
Create TAXON.MEDIOIDS matrix
FOR each TAXON.NAME
    Extract taxon-specific sub matrix from DIS.MAT
    Estimate column means of sub matrix
    Store vector of column means in TAXON.MEDIODS matrix
NEXT
Assign taxon names to rows and columns
Transpose TAXON.MEDIOIDS
Create TAXON.MEDIOIDS2 (square matrix)
FOR each taxon name
    Extract taxon-specific sub matrix from DIS.MAT
    IF only one vector occurs
        Store vector in TAXON.MEDIODS2 matrix
    ENDIF
    IF more than one vector occurs
        Estimate column means of sub matrix
        Store vector of column means in TAXON.MEDIODS2 matrix
    ENDIF
NEXT
NOTE - Restructure medioids by decremental column sort
Assign TAXON.MEDIOIDS2 to X
FOR (each row in X)-1
    Sort matrix column-wise in ascending order
    Assign name of first sequence to TAXON.NAME
    Reassign X to X[subtract first row, subtract first column]
NEXT
Identify the last sequence by comparing names of TAXON.MEDIOID2 with TAXON.NAME and add to TAXON.NAME
Reorder TAXON.MEDIOIDS2 by TAXON.NAME to yield a smoothed matrix of medioids.
STEP 12. - Restructure the dataset according to the plotting sequence of medioids.
```

Given a matrix of distances among the items to be classified and an initial hierarchical classification, the algorithm first restructures the matrix, so that the ordering of items in the matrix matches the ordering of items in the classification. Thus, members of a given group appear in the same region of the matrix and in close proximity to other items presumed to be members of the next higher group within the hierarchy. Next, the distance from each item to its second-nearest neighbor is extracted from the matrix and the $90^{th}$ percentile of this value is estimated. The $90^{th}$ percentile value serves as a "goodness-of-fit" (gof) measure and was chosen to provide a reasonable stringency, without being overly restrictive. In some embodiments, this value may be higher or lower (e.g., the $80^{th}$ percentile, the $70^{th}$ percentile, the $60^{th}$ percentile or lower, or the $91^{st}$ percentile, the $92^{nd}$ percentile, the $93^{rd}$ percentile, the $94^{th}$ percentile, the $95^{th}$ percentile or higher). Using the $90^{th}$ percentile gof value, a binary transformation of each submatrix, representing the distances among the members of a group, is then created and rearranged by hierarchical clustering along both dimensions of the matrix. These submatrices are then used to guide the global rearrangement of the complete input matrix, which may then be visualized (e.g., in some embodiments, visualized as a colorized distance matrix or, as it is also know, a heatmap).

In some embodiments of the present invention, in a further iteration, items that fail to meet the gof test (indicative of items that were misclassified in the original classification) are excluded from the analysis and the rearrangement of items is further refined using the above heuristic. On completion, the misidentified items can be added back to the "cleaned" matrix, and placed adjacent to their nearest neighbors, based on distance rather then the presumed identity from the original classification. The classification table is then revised based on the matches, and the sorting and visualization routine is repeated using the revised classification. The process is then repeated to test for any items that fail to meet the gof criterion, in their new location. Those items that fail to meet the gof criteria are then excluded from further analysis, as they are likely members of more distantly related groups that lie outside the natural boundaries of the group being studied.

To establish an optimal ordering for the grouped items at higher levels, a summary statistic, the medioid, was used for the distance from each group to the other groups. This statistic represents a distance from the hypothetical center of each group to the hypothetical centers of all the other groups. First, the column means from each group-level submatrix was estimated, effectively reducing the initial matrix from a square matrix to a rectangular matrix with the medioids on one axis and the items on the other. The matrix was then transposed and column means computer in a second iteration to yield a reduced matrix in which each group was represented by a single medioid in a vector of distances.

The matrix of medioids was subjected to a round of supervised sorting, as was performed at the group level, resulting in a rearrangement of the medioid matrix. In this pass, a smoothing routine was also introduced, which involved an iterative column sort (analogous to the process of seriation, See, e.g., Sneath and Sokal, Numerical Taxonomy, The Principles and Practice of Numerical Classification. W. H. Freeman, San Francisco, Calif., 1973) where the dimensions of medioid matrix were successively decreased by a single row and the column on each successive pass. The final ordering of medioids was then used to create a new index (using the order of appearance of each group) into the full distance matrix.

Example 2

Heatmap of the "Gammaproteobacteria" Based on an Evolutionary Distance Matrix with Unnamed and Uncorrected Sequences Removed The distances are encoded as indicated on the scale (See FIG. 1). Ordering of the sequences within the heatmap is based on the sequence of taxa in Outline of Prokaryotic Taxa, Release 3.0. Solid bars along the axis indicated the range encompassed by individual families within the heatmap. Families are as follows: Ectothiorhodospiraceae, Xanthomonadaceae, Cardiobacteriaceae, Thiotrichaceae, Piscirickettsiaceae, Franciscellaceae, Legionellaceae, Coxiellaceae, Methylococcaceae, Oceanospirillaceae, Alcanovoraxaceae, Halomondaceae, Pseudomonadaceae, Moraxellaceae, Alteromonadaceae, Vibrionaceae, Aeromonadaceae, Succinovibrionaceae, Enterobacteriacceae, Pasteurellaceae. Highlighted areas (See FIGS. 1a and 1b) indicate misplaced taxa.

Example 3

Figure 2:
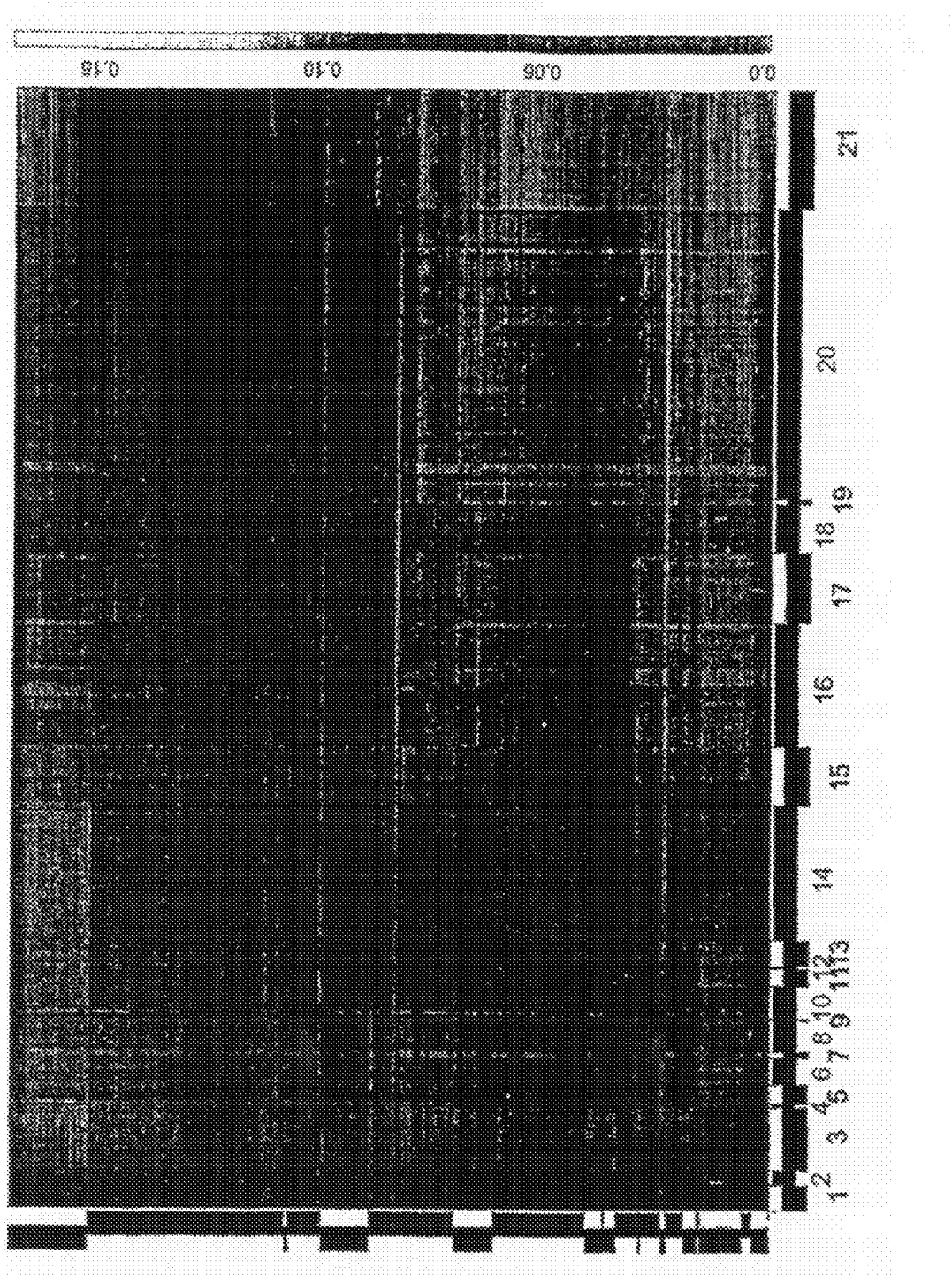
FIG. 2 shows an exemplary heat map of the "Gammaproteobacteria" with unnamed and uncorrected sequences added back following supervised clustering.

Heatmap of the "Gammaproteobacteria" with Unnamed and Uncorrected Sequences Added Back Following Supervised Clustering The heat map is re-created after reorganization of the genera and re-insertion of unnamed and misidentified sequences (See FIG. 2). The ordering of the families is according to the Outline of Prokaryotic Species and are ordered as in FIG. 1. The exclusion of a small number of sequences derived from species not belonging to the "Gammaproteobacteria" results in a significant decrease in the overall range of evolutionary distances within the matrix. This is reflected in the improved contrast observed between closely related and distantly related species, accentuating further classification problems. Inspection of the heat map shows that while clear errors in sequence placement have been corrected, ordering of the genera within the higher taxa, those within the families and orders of the "Gammaproteobacteria," remain suboptimal. Specifically, there exist three sharp breaks, two transecting the Alteromonadaceae and one transecting the Enterobacteriacceae. Similarly, the Xanthomonadaceae, Piscirickettsiaceae and Franciscellaceae appear misplaced, interrupting families that would otherwise be contiguous.

Example 4

Application of the Reordering Algorithm

Figure 3:
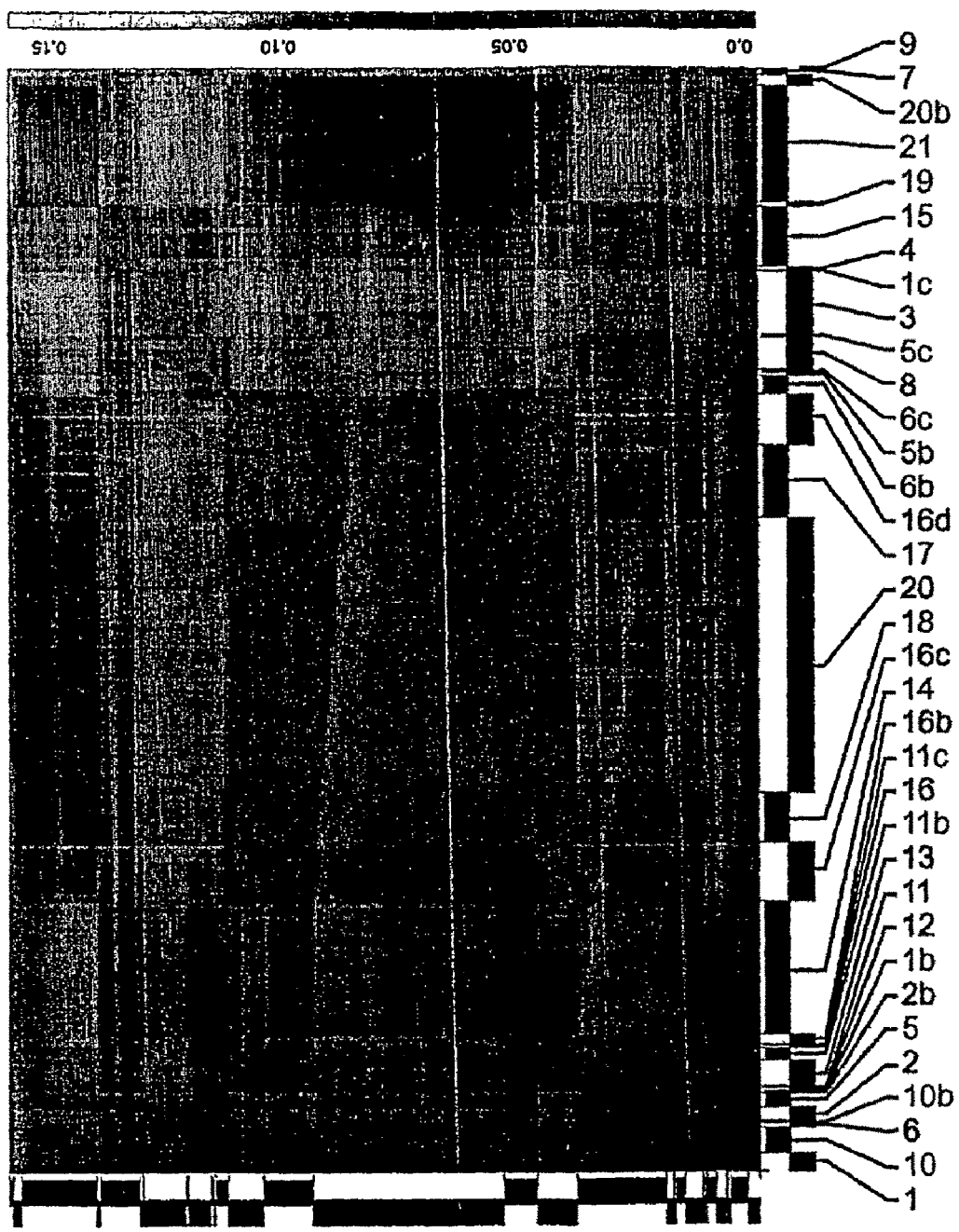
FIG. 3 shows an exemplary optimized heat map of the "Gammaproteobacteria" based on seriated medioids.

Application of the medioid reordering algorithm resolves the discrepancies observed in FIG. 2. The initial classification, in which the 125 genera were grouped into 21 families, is subdivided into 35 groups, suggesting that some of the families are paraphyletic (FIG. 3). While 13/21 families remained unchanged in composition, the remaining eight families are subdivided into two (Methylococcaceae, Ectothiorhodospiraceae, Enterobacteriaceae), three (Chromatiaceae, Oceanospirillaceae, Piscirickettsiaceae, Thiotrichaceae) or four (Alteromonadaceae) subgroups. Also evident is the location changes of the taxonomic groups Enterobacteriaceae, Xanthomonadaceae, and Moraxellaceae from their locations in the original map, as the algorithm orders taxa according to overall levels of similarity defined by 16S sequence analysis.

Example 5

Exploring Prokaryotic Taxonomy: Methods

Alignment. Alignments are based on the RDP-II Release 8.0 prokaryotic alignment (See, e.g., Maidak et al., Nucleic Acids Res., 29:173 (2001)). The alignment includes 200 sequences from type strains that are not found in Release 8.0. One thousand one hundred and one positions from the alignment were used; they were selected according to (i) the measured variability at each position and (ii) information presented in conservation maps that have been published (See, e.g., Cannone et al., BMC Bioinformatics, 3:2, Epub Jan. 17, 2002, Erratum in: BMC Bioinformatics. Jul., 3:15 (2002) and Wuyts et al., Nucleic Acids Res. 30:183-5 (2001)).

Sequence data. Relatively long prokaryotic sequences were used in the analyses in order to maximize the information content and to ensure that the sequences contained as many homologous positions as possible. The 9,206 sequences used were more than 1399 bases long and had less than 4% ambiguities. If sequences contained no data in more than 10 consecutive alignment positions, they were eliminated from the data set. The data was grouped and 223 benchmark sequences incorporated as discussed previously (See, e.g., Garrity & Lilburn, WFCC News1 35, 5-15 (2002)). In the benchmark set of sequences, each sequence represented, where possible, a type species and type genus on which the families are based (See, e.g., Garrity et al., *Taxonomic outline of the procaryotes*. Release 3.0, July 2002, available at: http:// dx.doi.org/10.1007/bergeysoutline). All 25 phyla in Bergey's taxonomic outline are represented.

Estimation of evolutionary distances. Prior to estimation of evolutionary distance, subsets of sequences were created, ranging from 750 to 900 sequences total. Each subset contained the benchmark sequences as the first 223 sequences. Matrices of evolutionary distances were calculated in PAUP* (Version 4.08) (Swofford, 2000) using the Jukes and Cantor model (See, e.g., Jukes & Cantor, Evolution of protein molecules. In *Mammalian Protein Metabolism*, pp. 21-132. Edited by H. N. Munro. New York: Academic Press (1969)). Following computation, each matrix was exported as a tab delimited file, using a short identifier to tag each sequence.

Data structures. Matrices of evolutionary distances were imported into the statistical package Splus 6.1, (Insightful), edited and joined in a single data frame and finally linked to a data frame containing taxonomic and physiological information, as described previously (See, e.g., Garrity & Lilburn, WFCC News1 35, 5-15 (2002)). By invoking functions that are part of the S-Plus, it was possible to arrange the sequence order on the axes of the matrix according to the current version of the taxonomy, based on the hierarchy of names, which were treated as ordered factor variables. Sequences without names were moved to the ends of the lists. The matrix was then color-coded to allow data patterns to be seen. This allows identification of any potential misplacements that arise because of incorrect annotation of sequences or because of a failure to identify synonyms.

In the next cycle, the misidentified sequences were extracted and arranged in a new matrix according to their similarities to the benchmark sequences. The unnamed benchmark sequences were also reordered.

Similar routines were carried out on two subsets of the data: sequences from the class "Betaproteobacteria" and from the family Comamonadaceae.

Example 6

Initial Heat Map Representing Two Million Distances

Figure 4:
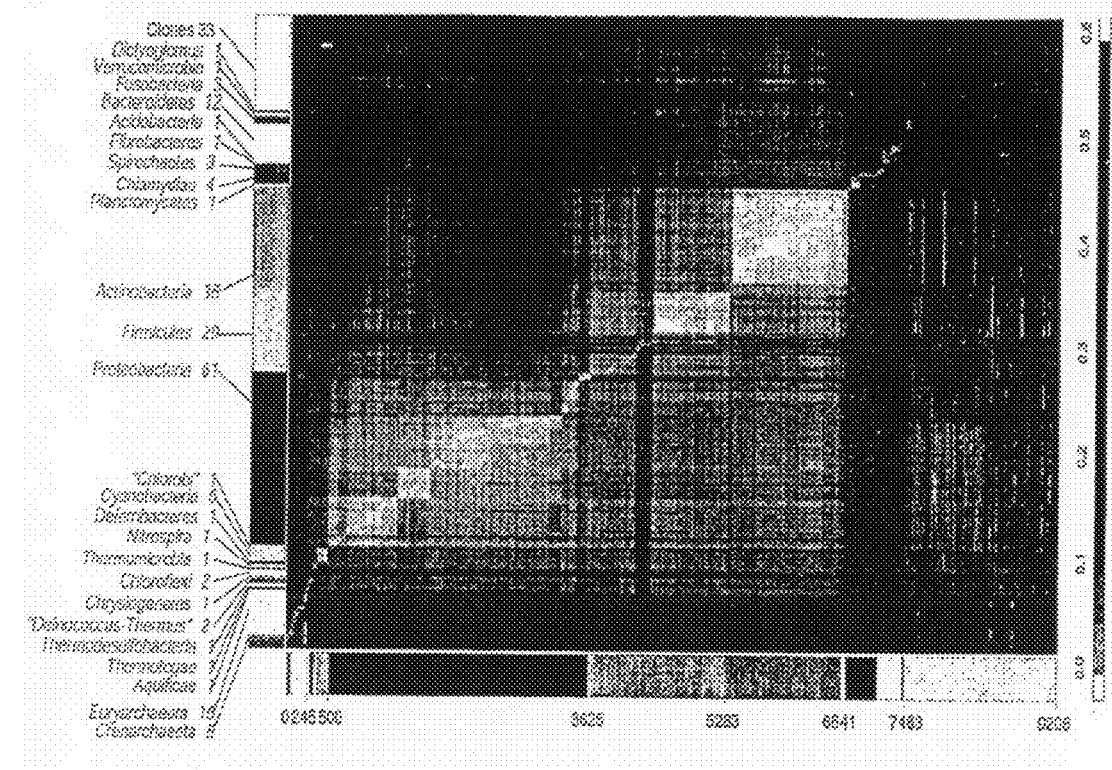
FIG. 4 shows an exemplary heat map representing the first-pass shaded distance matrix of the distances from 9,206 sequences in the data set to the 223 benchmark sequences.

An initial beat map representing over two million distances was created using 9206 sequences (See FIG. 4). Two hundred and twenty-three benchmark sequences, selected to represent the breadth of prokaryotic diversity are on the y-axis, clustered according to their position in the July 2002 Bergey's taxonomy. At y values>190 are sequences that (i) are from organisms not in culture at the time of publication and (ii) form deep branches within the RDP-II tree. On the x-axis are 9,206 sequences from the RDP-II and GenBank, also clustered by name according to their place in the taxonomy; sequences not associated with a named organism are placed at x values>7463. Since the benchmarks and bulk of the sequences are clustered according to the same hierarchy, the bright green color indicating the highest level of sequence similarity is seen on the diagonal between positions (0, 0) and (7463, 190). Misplaced sequences are seen as areas (rectangles) of color that contrast with the background color located off the diagonal and above the x coordinate corresponding to the misplaced sequence(s). For example, a misplaced sequence can be seen at y=200 as a red line extending across most of the plot (See FIG. 4). Beyond coordinates (7463, 190) the diagonal pattern breaks down. Sequences in this region could not be positioned based on known taxonomic affiliation because no name information was available.

Example 7

Identification and Classification of Unknown Sequences

Figure 5:
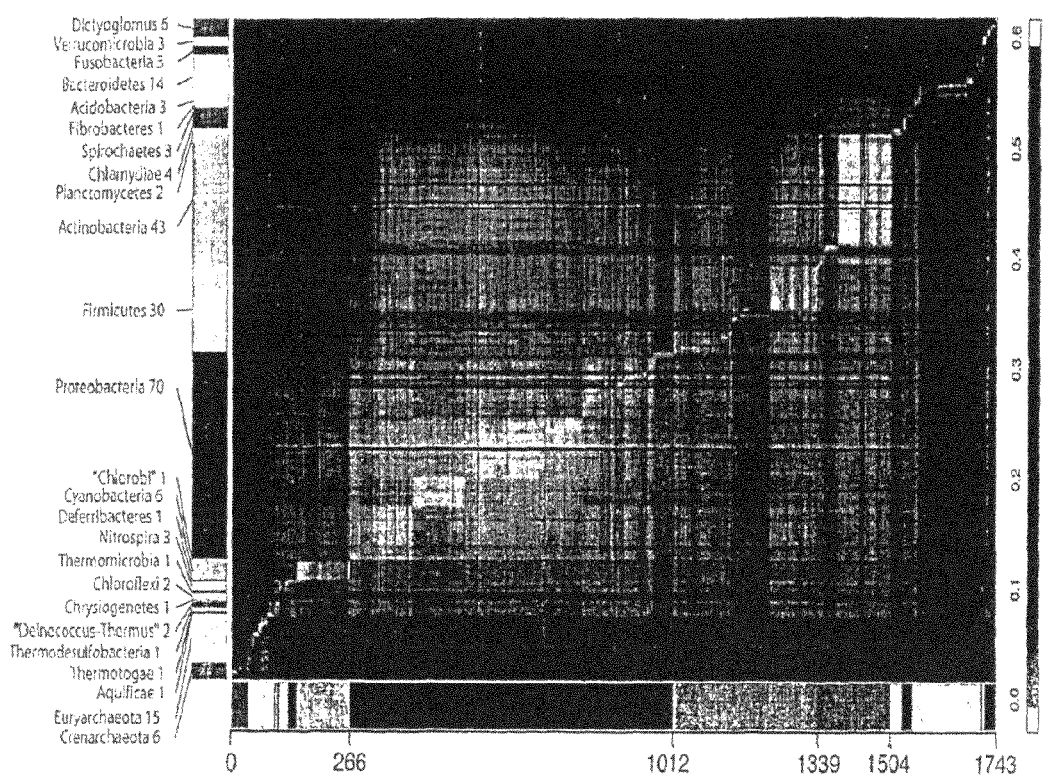
FIG. 5 shows an exemplary heat map representing the shaded distance matrix distances to the 223 benchmark sequences from the 1,743 sequences in the first matrix that could not be placed in the hierarchy due to a lack of nomenclatural information.

In order to identify and classify the unknown sequences, it was necessary to write a routine that, in essence, moved the unknown sequence along the x-axis until the element representing the highest similarity value for that sequence was placed on the diagonal of the heat map rectangle. The results of this type of re-ordering with the subset of "unnamed" sequences is shown (See FIG. 5). Note that the benchmark sequences have also been re-ordered so that each of the 33 unnamed benchmark sequences is positioned next to the sequence on the x-axis to which it is most similar. All of the sequences have now been successfully placed in a known phylum, although it is clear, from the dark lines that cross the heat map, that some of the sequences are from organisms that are only distantly related to the phylum in which they have been placed. In other words, the algorithm has forced them into a taxon that they may not actually belong in. There is also a problem with the visualization of the sequence placement. In phyla with low sequence diversity, such as the Actinobacteria, almost the entire block of sequences is a single shade of green and any problems of classification etc. at sub-phylum levels are masked.

Example 8

Figure 6:
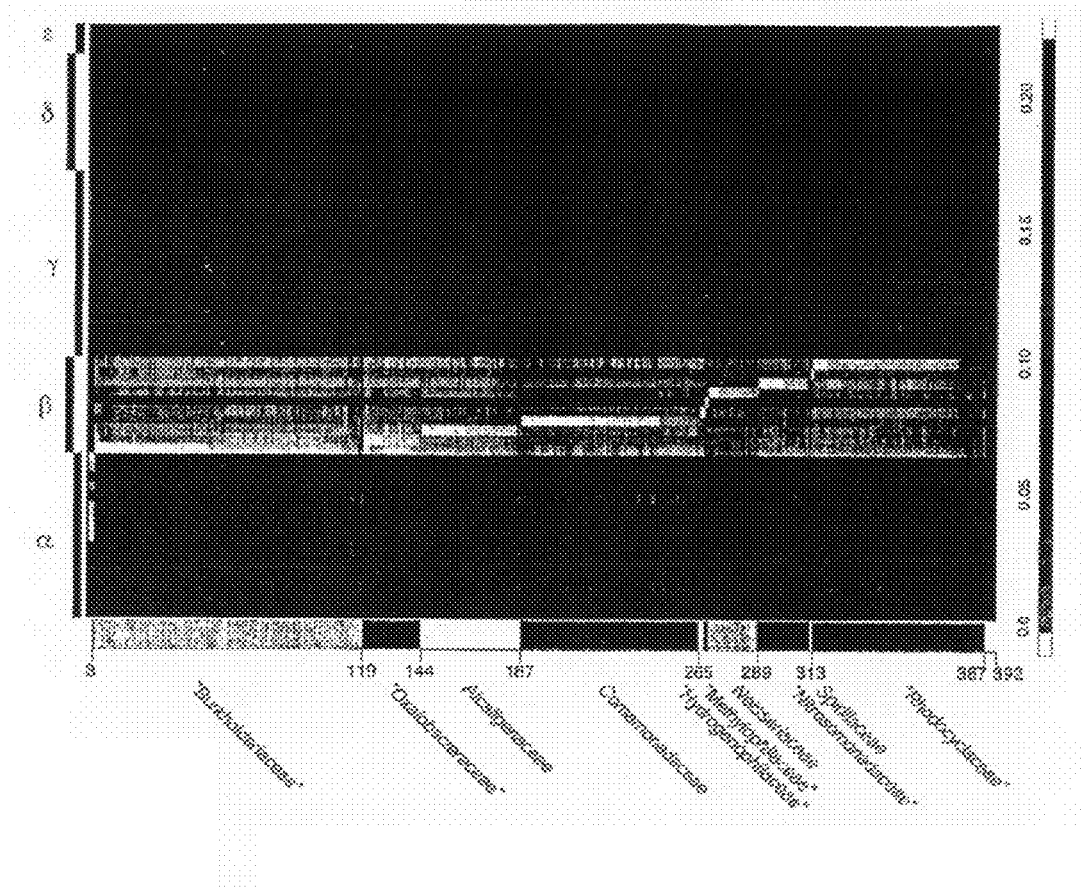
FIG. 6 shows an exemplary heat map representing the distances between the 61 Proteobacteria benchmarks and the 392 sequences in the data set classified as "Betaproteobacteria".

Classification of Sequences from the First Matrix that were not Placed Due to a Lack of Nomenclatural Information Restricting the view of the data to a subset of the data and resetting the color scale readily solved the difficulty of visualizing the sequence placement. When utilizing this solution with the "Betaproteobacteria", visualization of the taxonomy was possible and corrections were made as necessary down to the family level (See FIG. 6). Resolution below the family level relies to some extent on the simple visualization of distances, since the benchmarks were selected to represent the prokaryotic families and are therefore ineffectual below the family level.

Example 9

The Use of Heat Maps for the Revision of an Extant Taxonomy

Figure 7:
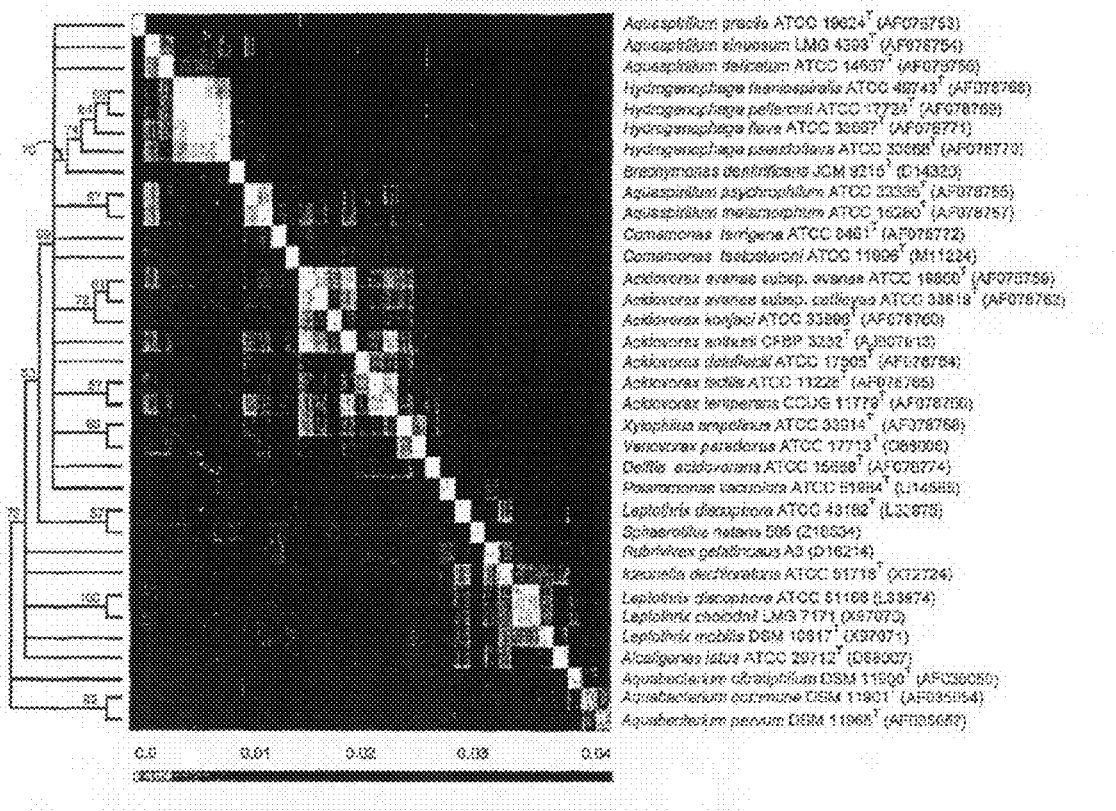
FIG. 7 shows an exemplary heat map representing the distances between 35 sequences from organisms that are or have been or may be members of the Family Conzamonadaceae.

The family Comamonadaceae is visualized along with sequences that once formed part of this family or that are proposed to form part of the family. Genera within the family can be seen. The sequences have been rearranged according to their order in a neighbor joining consensus tree. (See FIG. 7).

Example 10

The Use of Medioid Reordering

Use of medioid reording resolves additional discrepancies. Methods of the present invention conducted without medioid reording produced heat maps where errors in sequence placement were corrected. However, ordering of the genera within the higher taxa (e.g., within the families and orders of the Gammaproteobacteria) remained suboptimal. Particularly noteworthy were three sharp breaks: two transect the Alteromonadaceae and on transects the Enterobacteriaceae. Likewise, it was apparent that the Xanthomonadaceae, Piscirickettsiaceae, and Franciscellaceae seemed to be misplaced, interrupting families that would otherwise be contiguous. Application of the medioid reodering algorithm resolved most of these discrepancies.

All publications and patents mentioned in the above specification are herein incorporated by reference. Various modifications and variations of the described algorithm and methods of using the same of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method of classifying data; comprising:
   a) providing:
      i) a data set, wherein said data set comprises unique data points; and
      ii) software configured to run a self-organizing, self-correcting algorithm;
   b) inputting said data set into a processor running said algorithm;
   c) generating a classification of said data set, wherein said generating a classification
   of said data set comprises:
      i) removing data points not meeting a predetermined similarity criterion comprising a goodness-of-fit measure;
      ii) generating a first classification, wherein said first classification comprises
         a first classification plurality of groupings; wherein said first classification plurality of groupings comprise data points meeting said pre-determined similarity criterion that are related;
      iii) fitting said data points not meeting a pre-determined similarity criteria into
         said first classification; and
      iv) generating a second classification, wherein said second classification comprises a second classification plurality of groupings; wherein said second classification plurality of groupings comprise related:
         a) data points meeting a predetermined similarity criterion; and
         b) data points not meeting a pre-determined similarity criterion.

2. The method of claim 1, further comprising visualizing said first or second classification of said data set through a heat map.

3. The method of claim 1, wherein said data set comprises prokaryotic SSU rRNA sequences.

4. The method of claim 1, wherein said data set is selected from the group consisting of prokaryotic nucleic acid sequences, prokaryotic peptide sequences, eukaryotic nucleic acid sequences, eukaryotic peptide sequences, viral nucleic acid sequences, viral peptide sequences, nucleic acid sequences derived from cultured cells, and peptide sequences derived from cultured cells.

5. The method of claim 3, wherein said prokaryotic SSU rRNA sequences are specific for a prokaryotic organism.

6. The method of claim 1, further comprising identifying a classification of an unknown data point; wherein said identifying a classification of an unknown data point comprises:
   i) inputting said unknown data point into said processor running said algorithm; and
   ii) fitting said unknown data point into said second classification.

7. The method of claim 6, wherein said unknown data point is an unknown SSU rRNA sequence.

8. The method of claim 1, further comprising the step of subjecting said second classification to a medoid reordering algorithm to generate a third classification.

9. A system comprising software stored on a non-transitive computer medium to carry out the method of claim 1.

* * * * *